US012605569B2

(12) United States Patent
Penot et al.

(10) Patent No.: US 12,605,569 B2
(45) Date of Patent: Apr. 21, 2026

(54) PROCESS FOR TESTING THE ACCURACY AND THE PERFORMANCE OF AN ULTRASOUND TRANSDUCER

(71) Applicant: CARDIAWAVE, Levallois-Perret (FR)

(72) Inventors: Robin Penot, Levallois-Perret (FR); Daniel Suarez, Levallois-Perret (FR); Mathieu Remond, Levallois-Perret (FR); Wojciech Kwiecinski, Levallois-Perret (FR)

(73) Assignee: CARDIAWAVE, Levallois-Perret (FR)

( * ) Notice: Subject to any disclaimer, the term of this patent is extended or adjusted under 35 U.S.C. 154(b) by 325 days.

(21) Appl. No.: 18/032,550

(22) PCT Filed: Oct. 22, 2021

(86) PCT No.: PCT/EP2021/079430
§ 371 (c)(1),
(2) Date: Apr. 18, 2023

(87) PCT Pub. No.: WO2022/084547
PCT Pub. Date: Apr. 28, 2022

(65) Prior Publication Data
US 2023/0381544 A1     Nov. 30, 2023

(30) Foreign Application Priority Data
Oct. 23, 2020    (EP) .................................... 20306276

(51) Int. Cl.
*A61N 7/00*      (2006.01)
*A61B 8/00*      (2006.01)
(Continued)

(52) U.S. Cl.
CPC ................ *A61N 7/00* (2013.01); *A61B 8/587* (2013.01); *A61B 17/22004* (2013.01); *A61B 17/225* (2013.01); *A61N 2007/0039* (2013.01)

(58) Field of Classification Search
CPC .............. A61N 7/00; A61N 2007/0039; A61B 17/22004; A61B 17/225; A61B 8/587
See application file for complete search history.

(56) References Cited

U.S. PATENT DOCUMENTS 5,755,228 A     5/1998   Wilson et al.
7,255,565 B2    8/2007   Keegan
(Continued)

FOREIGN PATENT DOCUMENTS

CN      104 225 810 A    12/2014
CN      107540786 A   *   1/2018
(Continued)

OTHER PUBLICATIONS

Khokhlova et al., "Effects of nonlinear propagation, cavitation, and boiling in lesion formation by high intensity focused ultrasound in a gel phantom", Journal of Acoustical Society of America, 119, pp. 1834-1848, 2006 (Year: 2006).*
(Continued)

*Primary Examiner* — Stephen D Meier
*Assistant Examiner* — Quang X Nguyen
(74) *Attorney, Agent, or Firm* — BakerHostetler

(57) ABSTRACT
A method for testing the accuracy and the performance of an ultrasound transducer able to generate cavitation bubbles by placing in a volume of an ultrasound-transmitting medium an elastomer block at an expected cavitation region of the ultrasound transducer, activating the ultrasound transducer so as to generate cavitation bubbles in the elastomer block, detecting in the elastomer marks corresponding to the generated cavitation bubbles and deducing from the marks the three-dimensional characteristics of a real cavitation region of the ultrasound transducer. A system comprising volume of an ultrasound-transmitting medium, an elastomer block dis-
(Continued)

10

14

19

11

12

13

15 posed in the volume of an ultrasound-transmitting medium, and an ultrasound transducer is also provided.

17 Claims, 3 Drawing Sheets

(51) Int. Cl.
| | |
|---|---|
| *A61B 17/22* | (2006.01) |
| *A61B 17/225* | (2006.01) |

(56) References Cited

U.S. PATENT DOCUMENTS

| | | | | |
|---|---|---|---|---|
| 8,539,813 | B2 | 9/2013 | Cain et al. | |
| 9,743,909 | B1 | 8/2017 | Sapozhnikov et al. | |
| 2005/0227364 | A1* | 10/2005 | Madsen ................... | A61B 8/08 |
| | | | | 436/80 |
| 2011/0067624 | A1* | 3/2011 | Cain .................... | G09B 23/286 |
| | | | | 116/203 |

| | | | | |
|---|---|---|---|---|
| 2011/0076660 | A1 | 3/2011 | Morris et al. | |
| 2013/0090579 | A1* | 4/2013 | Cain ........................ | A61N 7/00 |
| | | | | 601/2 |
| 2014/0356967 | A1 | 12/2014 | Kawabata et al. | |

FOREIGN PATENT DOCUMENTS

| | | | |
|---|---|---|---|
| JP | 2005-118187 | A | 5/2005 |
| JP | 2011-72779 | A1 | 4/2011 |
| WO | 2013/099787 | A1 | 7/2013 |
| WO | 2020/113083 | A1 | 6/2020 |

OTHER PUBLICATIONS

Alves et al., "Cardiac Tissue-Mimicking Ballistic Gel Phantom for Ultrasound Imaging in Clinical and Research Applications", Ultrasound in Medicine and Biology, vol. 46, No. 8, pp. 2057-2069, Aug. 2020 (Year: 2020).*

English translation of the Notice of Reasons for Rejection issued in Japanese Patent Application No. 2023-524844 dated Jul. 8, 2025.

* cited by examiner 10
14
19
11
12
13
15

20
24
29
22
27
21
23
25
28
26

42

43

PROCESS FOR TESTING THE ACCURACY AND THE PERFORMANCE OF AN ULTRASOUND TRANSDUCER

CROSS-REFERENCE TO RELATED APPLICATIONS

This application is a National Stage of International patent application PCT/EP2021/079430, filed on Oct. 22, 2021, which claims priority to foreign European patent application No. EP 20306276.5, filed on Oct. 23, 2020, the disclosures of which are incorporated by reference in their entirety.

FIELD OF THE INVENTION

The present invention relates to a process for testing the accuracy and the performance of an ultrasound transducer by causing the generation of cavitation bubbles in an elastomer. The present invention also relates to a system comprising a volume of an ultrasound-transmitting medium, an ultrasound transducer and an elastomer block being disposed within the volume of an ultrasound-transmitting medium.

BACKGROUND PRIOR ART

Interest in technologies using ultrasonic waves has grown steadily as numerous potential applications have been discovered. Ultrasonic waves may be used to induce cavitation bubbles by focusing ultrasound pulses at a focal spot, allowing the release of mechanical energy towards a specific target in a region included, partially included or close to the focal spot. Multiple cavitation bubbles may be generated in such region close to or at the focal spot, which may therefore be identified as a cavitation region. The cavitation bubbles induced may be referred to as a cavitation cloud. Cavitation bubbles or cloud generated by ultrasonic waves may be used for medical applications, such as histotripsy (the mechanical destruction of tissues), thrombotripsy (mechanical destruction of thrombi) and lithotripsy (fragmentation of calculi), such applications having the particular advantage of being non-invasive.

Such applications of focused ultrasound pulses require a high level of precision regarding the focal spot and the cavitation region where the cavitation bubbles or cloud will be generated, especially with medical applications. Assessment and characterization of the position and/or the dimensions of the cavitation region remain challenging as the expected cavitation region may be changed according to the target and according to the position of the apparatus. It is particularly important to ensure that the expected cavitation region, which corresponds to the location where cavitation bubbles are expected to be generated, is the closest to a real cavitation region, which corresponds to the location where cavitation bubbles are generated, with minimal uncertainty.

A straightforward solution is to test the ultrasound transducer in vitro before using it for a treatment procedure, placing at the expected cavitation region a target which may be damaged by the cavitation bubbles generated. However, although ensuring that at least cavitation has been generated at the expected cavitation region in the case the target is damaged, such method does not allow assessing reliably the three-dimensional characteristics of a real cavitation region. Therefore, such method is not precise enough to ensure the reliability of the method for a treatment procedure.

U.S. Pat. No. 8,539,813 discloses a cavitational damage indicator phantom comprising a container, a gel disposed in the container and an indicator disposed in the container, the indicator configured to change visibly during application of cavitational ultrasound energy to the indicator. The indicators disclosed comprise microspheres or polystyrene beads, microencapsulated beads, or carbon particles. The visible change corresponds to the particle becoming darker or their size being reduced, or a pigment being spilled. However, these visible changes do not provide enough information to assess the three-dimensional characteristics of a real cavitation region as the indicators are present in a single layer and therefore provide only limited three-dimensional information. If the ultrasound transducer is used with an increased pulsed repetition frequency with long duration at an important central frequency, the structure of the indicator may be insufficiently resistant and may tear apart. Hence the visible changes would correspond to a tear in the indicator which would provide none or misleading information on a real cavitation region.

There is therefore the need for a process and a system which allow identifying more precisely a real cavitation region where cavitation bubbles will be generated. Moreover, it is particularly important to reliably determine the position and/or the three-dimensional characteristics of a real cavitation region as procedures using an ultrasound transducer may comprise an emission sequence of ultrasonic waves with an expected cavitation region which is displaced during the emission sequence and/or with transducer parameters which vary during the emission sequence. The invention seeks to overcome the aforementioned drawbacks of the prior art as it aims to provide a process for testing an ultrasound transducer based on more reliable information regarding the correspondences of the expected cavitation region and a real cavitation region, so as to ensure the accuracy and the performance of the ultrasound transducer.

SUMMARY OF THE INVENTION

To this effect the invention discloses a method of testing the accuracy and the performance of an ultrasound transducer able to cause the generation of cavitation bubbles comprising: placing in a volume of an ultrasound-transmitting medium an elastomer block at an expected cavitation region of the ultrasound transducer; activating the ultrasound transducer so as to generate cavitation bubbles in the elastomer block; detecting in the elastomer block marks corresponding to the generated cavitation bubbles; deducing from the marks a real cavitation region of the ultrasound transducer.

Advantageously, the elastomer block has a total optical transmittance of at least 20%. Such a percentage of total optical transmittance allows observing visible changes in the elastomer with the naked eye when cavitation bubbles have been generated. Preferably, the total optical transmittance is of at least 50%, or even more preferably of at least 95%.

Advantageously, the elastomer block comprises a material chosen among a silicone, urethane, polyurethane or a combination thereof.

Advantageously, the method comprises a step of verifying the correct alignment of one or more imaging systems with the ultrasound transducer.

Advantageously, the elastomer block has a hardness comprised between Shore hardness 10A and Shore hardness 80D, preferably between Shore hardness 30A and Shore hardness 80D, even more preferably between Shore hardness 30A and Shore hardness 95A. The preferred hardness of the elastomer block is comprised between Shore hardness 30A and Shore hardness 35A.

Advantageously, the method further comprises a plurality of graduation elements embedded in the elastomer block, said graduation elements being resistant to distortion or mechanical damage by the generated cavitation bubbles.

Advantageously, the graduation elements are wires or markers visible to the naked eye and/or visible with imaging modalities, preferably medical imaging modalities. By imaging modalities, it is understood imaging methods using X-ray, computed tomography, ultrasound imaging or magnetic resonance imaging. These imaging modalities may comprise one or more imaging systems which may comprise an imaging probe. For instance, the wires or markers may be echogenic to allow their observation by echography, and/or opaque to X-rays to allow their observation by radiology. By "graduation elements" is meant any type of element allowing the comparison of these elements with marks formed in the elastomer block so as to determine the three-dimensional characteristics of a real cavitation region. In particular, graduation elements may correspond to elements regularly spaced in the elastomer block.

Advantageously, the ultrasound-transmitting medium is liquid or semi-liquid and contained within a vessel.

Alternatively, the volume of ultrasound-transmitting medium forms a solid block comprising an access port, the access port being adapted for exposing a portion of a surface of the elastomer block to ultrasounds emitted by the ultrasound transducer.

Advantageously, the solid block further comprises at least one opening, the at least one opening being adapted for seeing and/or replacing the elastomer block.

Advantageously, the ultrasound transducer is a therapy ultrasound transducer.

The invention also discloses a system comprising a volume of an ultrasound-transmitting medium comprising an acoustic coupling medium, an elastomer block being disposed in the volume of an ultrasound-transmitting medium, an ultrasound transducer, the ultrasound transducer being mounted on a support structure so as for the ultrasound transducer to be within the acoustic coupling medium or acoustically coupled with the volume of an ultrasound-transmitting medium.

Advantageously, the system further comprises one or more imaging systems.

Advantageously, the ultrasound-transmitting medium of the system is liquid or semi-liquid and contained within a vessel.

Alternatively, the volume of an ultrasound-transmitting medium forms a solid block comprising an access port, the access port being adapted for exposing a portion of a surface of the elastomer block to ultrasounds emitted by the ultrasound transducer.

Advantageously, the solid block further comprises at least one opening, the at least one opening being adapted for seeing and/or replacing the elastomer block.

Advantageously, at a temperature of 25° C. and a pressure of 1 atm, the speeds of sound in the volume of ultrasound-transmitting medium and in the elastomer block are comprised between 500 m·s$^{-1}$ and 2500 m·s$^{-1}$ and are no more than 10% different, even more preferably between 1200 m·s$^{-1}$ and 1800 m·s$^{-1}$ and are no more than 5% different, and/or the acoustic impedances of the volume of ultrasound-transmitting medium and of the elastomer block are comprised between 0.5 MRayl to 2.5 MRayl and are no more than 10% different, even more preferably between 0.8 MRayl to 2.1 MRayl and are no more than 5% different.

Additionally and preferably, the acoustic attenuations in the volume of ultrasound-transmitting medium and in the elastomer block are below 20 dB·cm$^{-1}$·MHz$^{-1}$ and are no more than 20% different, even more preferably below 1 dB·cm$^{-1}$·MHz$^{-1}$ and are no more than 20% different.

Advantageously, the ultrasound transducer of the system is a therapy ultrasound transducer.

Advantageously, the system further comprises a plurality of graduation elements embedded in the elastomer block, said graduation elements being resistant to distortion or mechanical damage by the generated cavitation bubbles.

Advantageously, the material of the solid block is chosen among urethane, hydrogel polymer, or a combination of at least two of these materials.

BRIEF DESCRIPTION OF THE DRAWINGS

The invention will be better understood and its various characteristics and advantages will emerge from the following description of a number of exemplary embodiments and its appended figures in which.

DETAILED DESCRIPTION OF THE INVENTION

In this specification, the invention will be described by way of examples. However, the invention is not restricted to these examples.

Figure 1:
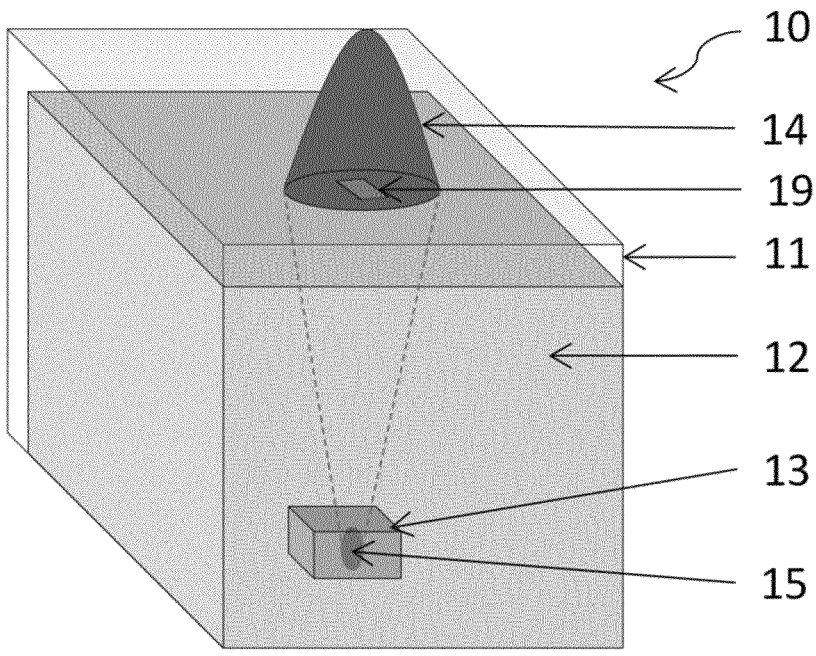
FIG. 1 displays a system comprising a volume of an ultrasound-transmitting medium which is liquid or semi-liquid and contained within a vessel, an elastomer block disposed in the volume of an ultrasound-transmitting medium and a transducer.

FIG. 1 displays a system 10 comprising a volume of an ultrasound-transmitting medium 12 which is liquid or semi-liquid and contained within a vessel 11 comprising an acoustic coupling medium, an elastomer block 13 disposed in the volume of an ultrasound-transmitting medium at the expected cavitation region 15 and an ultrasound transducer 14 with an imaging probe 19 of an imaging system.

As illustrated on FIG. 1, the vessel 11 has a parallelepiped shape but other shapes are possible, such as for instance cylinders of revolution, cones or a trapezoid shape. Typically, the vessel is made of transparent glass so as to see through the vessel faces but other materials are possible. Typically, the upper face of the vessel is open and allows placing or removing the elastomer block from the inside of the vessel, however other shapes are possible.

The vessel 11 comprises a volume of an ultrasound-transmitting medium 12 comprising an acoustic coupling medium. Typically, the volume of an ultrasound-transmitting medium fills the entire volume of the vessel but the vessel may also be only partially filled. The liquid or semi-liquid ultrasound-transmitting medium may be water although other ultrasound-transmitting medium, such as deaerated or degassed water or ultrasound gel. The choice of the ultrasound-transmitting medium to use depends on the environment in which it is desired to use the ultrasound transducer after testing. In the case the ultrasound transducer will further be used for therapy on a patient, the volume of an ultrasound-transmitting medium will most likely be chosen so as to have the same acoustic characteristics as a human body would have. The acoustic coupling medium allows coupling the ultrasound transducer with the volume of an ultrasound-transmitting medium and is generally water although other acoustic coupling medium may be used. For instance, the acoustic coupling medium may be deaerated or degassed water or ultrasound gel.

As illustrated on FIG. 1, the elastomer block 13 has a parallelepiped shape and is disposed inside the volume of an ultrasound-transmitting medium 12 but other shapes are possible, such as for instance cylinders of revolution, cones or a trapezoid shape.

Preferably, the elastomer block has a total optical transmittance of at least 20%, even more preferably at least 50%.

The elastomer block dimensions are larger than the wavelength of the ultrasound waves emitted by the transducer and preferably much larger, for instance the elastomer block is at least 1 cm*1 cm*1 cm. The elastomer block dimensions may be adapted so as to entirely encompass the path of the expected cavitation region when such expected cavitation region is moved during use of the ultrasound transducer.

The elastomer block has a hardness comprised between Shore hardness 10A and Shore hardness 80D, preferably between Shore hardness 30A and Shore hardness 80D, even more preferably between Shore hardness 30A and Shore hardness 95A. The preferred hardness of the elastomer block is comprised between Shore hardness 30A and Shore hardness 35A.

As illustrated in FIG. 1, the elastomer block 13 is disposed at the expected cavitation region 15 of the ultrasound transducer 14, e.g. a surface of the elastomer block is exposed to the ultrasounds emitted by the ultrasound transducer so as for the expected cavitation region to be situated inside the volume of the elastomer block. The expected cavitation region corresponds to the region at which multiple cavitation bubbles are expected to be generated according to a specific configuration of the ultrasound transducer, and therefore typically corresponds to a targeted part of the elastomer block. A real cavitation region corresponds to the location at which multiple cavitation bubbles have been generated in the elastomer block in a specific configuration of the ultrasound transducer. Therefore, in the case the ultrasound transducer is already correctly calibrated while performing the method of the invention, the expected cavitation region position is identical to said real cavitation region position. In the case the ultrasound transducer is not correctly calibrated while performing the method of the invention, said real cavitation region position may correspond to a part of the elastomer block which is different from the targeted part of the elastomer block. For instance, said real cavitation region may be adjacent to the expected cavitation region position.

In some embodiments, the ultrasound transducer may have its focal spot be moved. The focal spot may for instance be moved electronically or mechanically in a volume, for instance by changing the configuration of the ultrasound transducer. In such a case, the elastomer block is placed at the expected cavitation region for a specific configuration of the ultrasound transducer. The activation of the ultrasound transducer may be repeated multiple times according to multiple different configurations and therefore according to multiple different focal spots. Therefore, it is possible to test the ultrasound transducer according to the multiple configurations while the focal spot is moved between each configuration.

As illustrated in FIG. 1, the system comprises an imaging probe 19 of an imaging system. The imaging system allows imaging the zone surrounding the expected cavitation region, i.e. the elastomer block and what surrounds the elastomer block. The imaging system allows detecting in the elastomer block the marks formed by the cavitation cloud or bubbles generated by the ultrasound transducer although the step of detecting marks may also be carried out with the naked eye. Typically, the imaging system is an ultrasound imaging system but other imaging modalities may be used, such as imaging methods using X-ray, computed tomography, or magnetic resonance imaging. Using an imaging system for testing the ultrasound transducer allows verifying the correct alignment of the imaging system with the ultrasound transducer and with a real cavitation region. Typically, the step of verifying the correct alignment of an imaging system with the ultrasound transducer is carried out after the step of detecting in the elastomer block marks, or after the step of deducing from the marks the position of a real cavitation region of the ultrasound transducer.

Figure 2:
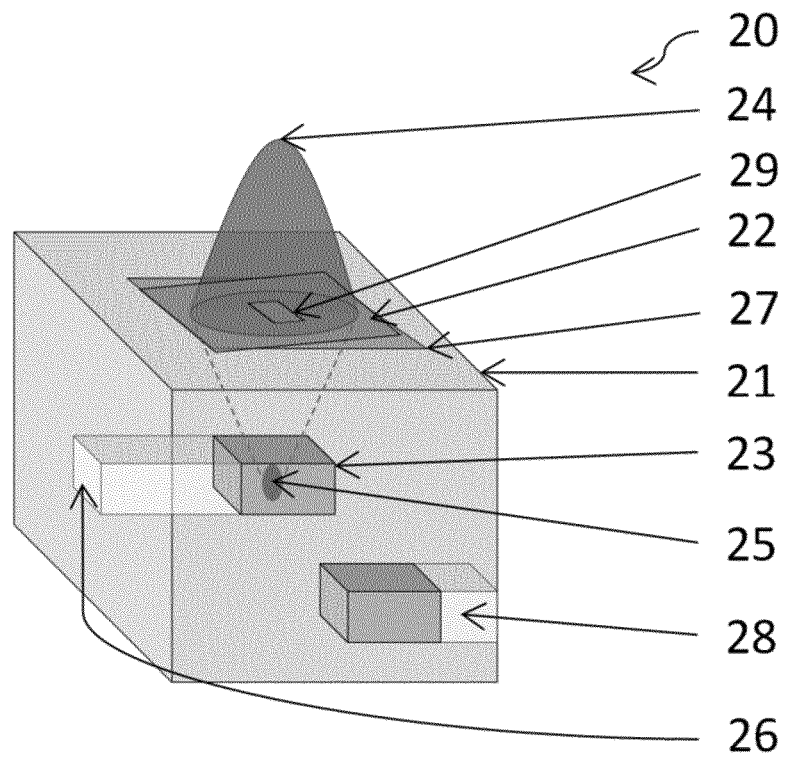
FIG. 2 displays a system comprising a volume of an ultrasound-transmitting medium which is a solid block and an elastomer block disposed in the solid block.

FIG. 2 displays a system 20 comprising a volume of ultrasound-transmitting medium forming a solid block 21, an elastomer block 23 disposed in the solid block, an ultrasound transducer 24 and an imaging probe 29 of an imaging system. The elastomer block is disposed at the expected cavitation region 25. The solid block 21 has a parallelepiped shape although other shapes may be used, such as for instance cylinders of revolution or cones or a trapezoid shape. The solid block may also have an irregular shape, with recesses or protuberances. In some embodiments, the solid block has a shape which mimics a part of a human body.

As illustrated in FIG. 2, the solid block 21 comprises an access port 27 on a first face of the solid block. The access port is adapted for exposing a portion of a surface of the elastomer block 23 to ultrasounds emitted by the ultrasound transducer. The access port may have a square shape but other shapes are possible such as a circle shape for instance. Advantageously, the shape of the access port corresponds to the shape of the ultrasound transducer so as to be a plug-in interface with the ultrasound transducer.

As illustrated on FIG. 2, the solid block 21 is hollow and the hollow of the solid block comprises the acoustic coupling medium 22. The solid block may also comprise protuberances extending from the internal faces of the solid block towards the internal part of the solid block, the protuberances being arranged for holding the elastomer block 23 inside the solid block.

Typically, the solid block 21 is in silicone, polyurethane, urethane, hydrogel polymer, compatible ultrasound fluid or a combination thereof although other materials may be used. In an embodiment, at least one face of the solid block is transparent. In an embodiment, the solid block is made of one or more materials which mimic a part of a human body.

As illustrated on FIG. 2, on a second face of the solid block 21 which is perpendicular to the first face, the solid block comprises an opening 26. The opening has a square or rectangular shape and corresponds to the size and shape of the elastomer block 23, allowing replacing the elastomer block in the solid block. The opening 26 also allows seeing the elastomer block from outside of the solid block when the elastomer block is disposed inside the solid block. Also illustrated on FIG. 2, the solid block comprises a second opening 28 on a third face of the solid block, the opening being filled with a second elastomer block or a compatible acoustic coupling medium.

In some embodiments, the access port 22 and the opening 26 are on the same face of the solid block 21. In other embodiments, the access port and the opening are on opposed faces, although other configurations are possible.

In some embodiments, the solid block 21 may further comprise additional openings for seeing or replacing the elastomer block 23, these additional openings being on the same face or different faces of the solid block than the access port 27 and the opening 26.

In some embodiments, the solid block is hollow and may be filled with an acoustic coupling medium. In the case the acoustic coupling medium is liquid, the liquid may exit the solid block from the opening. In such embodiments, the elastomer block is placed through the opening and fills the opening so as to prevent the liquid from exiting through the opening. In other embodiments, the shape of the solid block is such that the at least one opening leads to a cavity inside the solid block which does not communicate with the hollow of the solid block comprising the acoustic coupling medium. In such embodiment, the elastomer block is therefore almost completely surrounded by the solid block and the acoustic coupling medium cannot exit from the solid block through the opening as they do not communicate with each other.

In even further embodiments, the solid block has the shape of a part of a human body which mimics one or more tissues, e.g. bone and skin tissues, is filled with an acoustic coupling medium which mimics one or more other tissues, and has an opening for replacing the elastomer block at the expected cavitation region.

Figure 3:
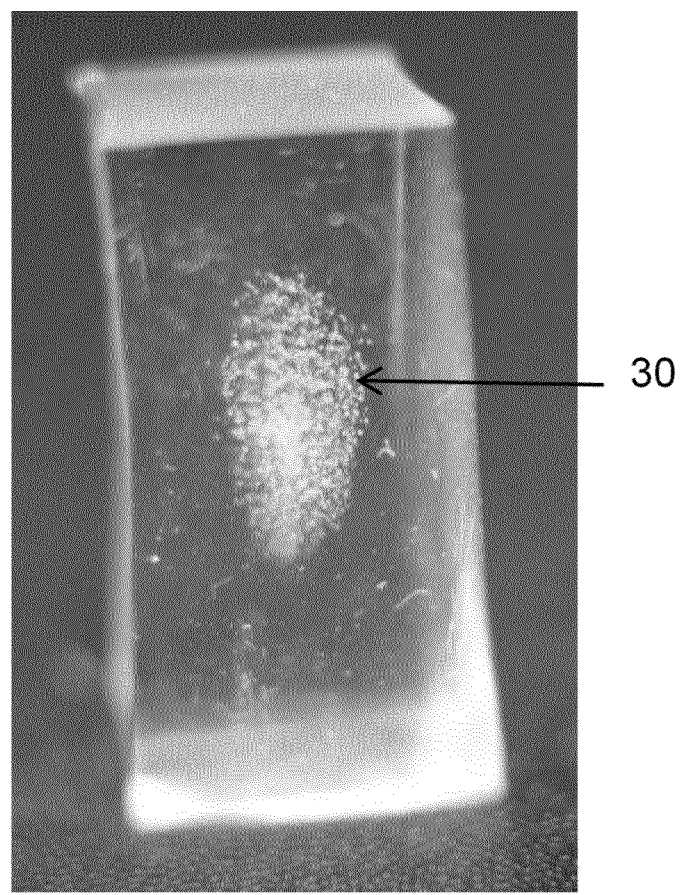
FIG. 3 displays an elastomer block on which cavitation bubbles have been generated, forming cavitation marks.

FIG. 3 displays an elastomer block on which cavitation bubbles have been generated, forming marks. The elastomer block of FIG. 3 has a parallelepiped shape and has a total optical transmittance of 95% which allows seeing with the naked eye marks of cavitation bubbles generated within its body by the focused ultrasonic waves. Marks 30 of cavitation bubbles generated in the elastomer block form a cavitation cloud having an oval shape and are entirely comprised in the volume of the elastomer block. In some embodiments, the marks of cavitation bubbles or cloud may have different shapes depending on the configuration of the ultrasound transducer, the material of the elastomer block and of the volume of an ultrasound-transmitting medium, and the acoustic coupling medium. The marks formed by the cavitation bubbles generated do not allow observing the entire cavitation region but only a central part of the cavitation region where the intensity of the ultrasound waves is the highest. Such central part of the cavitation region corresponds to the region where marks may appear in the elastomer block and therefore corresponds to what is referred in this description as a real cavitation region.

In particular, it must be noted that the marks in the elastomer block may be easily assessed in three dimension with the naked eye and without the use of a specific indicator or compound which, by its effusion, would bring to the fore a zone wherein multiple cavitation bubbles have been generated.

According to the present invention, the elastomer block may comprise graduation elements embedded in the elastomer block, said graduation elements being resistant to distortion or mechanical damage by the generated cavitation bubbles. By "graduation elements" is meant any type of element allowing the comparison of these elements with marks formed in the elastomer block so as to determine the three-dimensional characteristics of a real cavitation region.

In particular, graduation elements may correspond to elements regularly spaced in the elastomer block.

In some embodiments, the graduation elements are arranged one after the other in the measuring direction at equal intervals, forming a measurement scale which allows determining the size of a real cavitation region in the elastomer block. The graduation elements may be in the bulk of the elastomer block or may be disposed on one or more surfaces of the elastomer block. In some embodiments, the graduation elements are disposed on an entire cross section of the elastomer block. In some embodiments, the graduation elements are disposed so as to measure the length of a real cavitation region along the axis direction of the ultrasound transducer and/or perpendicularly to the axis direction of the ultrasound transducer.

In some embodiments, the graduation elements are disposed on a surface of the elastomer block which is seeable from the exterior of the solid block through the opening of the solid block.

In some embodiments, the graduation elements correspond to wires. The wires may be made of any material which is resistant to distortion or mechanical damage by the generated cavitation bubbles. The wires may be arranged so as form a grid.

Figure 4A:
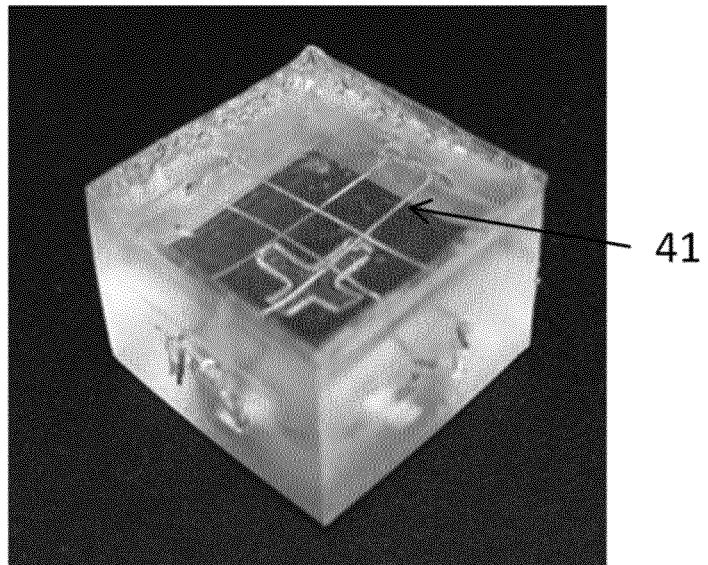
FIG. 4a displays an elastomer block comprising wires as embedded graduation elements forming a square.

FIG. 4a displays an elastomer block comprising wires 41 which are visible to the naked eye and which form a square. As may be seen from FIG. 4a, wires are embedded in the elastomer block essentially in a single plan so as to form a square at the centre of the elastomer block. Such square may correspond to a target. Therefore, the elastomer block may be placed in volume of an ultrasound-transmitting medium so as for the expected cavitation region to be in the square formed by the wires.

In particular embodiments, the graduation elements correspond to wires or markers visible with imaging modalities, for instance the wires being echogenic wires. An imaging probe of an imaging system, which may be embedded in the ultrasound transducer, may therefore identify the target formed by the wires or markers with ultrasound imaging. Other imaging modalities than ultrasound imaging may be used, such as computed tomography and magnetic resonance imaging. Further to the testing of the ultrasound transducer, such a system with wires or markers visible in the elastomer block with such imaging modalities allows verifying that the imaging modalities are correctly aligned with the ultrasound transducer and a real cavitation region.

Additionally, the ultrasound transducer may be connected to a mechatronic or robotic arm which may move the ultrasound transducer. A system of the present invention allows verifying that a movement of the ultrasound transducer due to the movement of the mechatronic or robotic arm corresponds to the movement of the real cavitation region, by deducing from the marks formed in the elastomer block if the expected cavitation region corresponds to a real cavitation region.

Figure 4B:
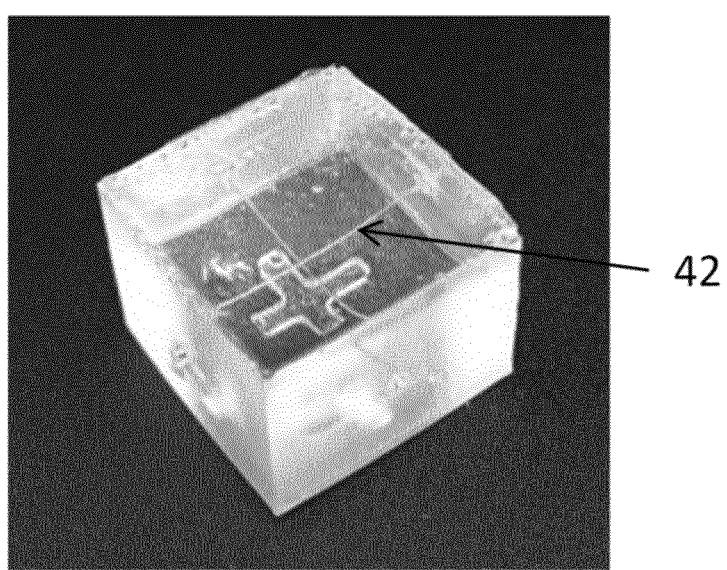
FIG. 4b displays an elastomer block comprising wires as embedded graduation elements forming a cross.

FIG. 4b displays an elastomer block comprising wires 42 which are visible to the naked eye and which form a cross. As may be seen from FIG. 4b, wires are embedded in the elastomer block essentially in a single plan so as to form a cross at the centre of the elastomer block. Such cross may correspond to a target. Therefore, the elastomer block may be placed in the volume of an ultrasound-transmitting medium so as for the expected cavitation region to be the centre of the cross formed by the wires.

Figure 4C:
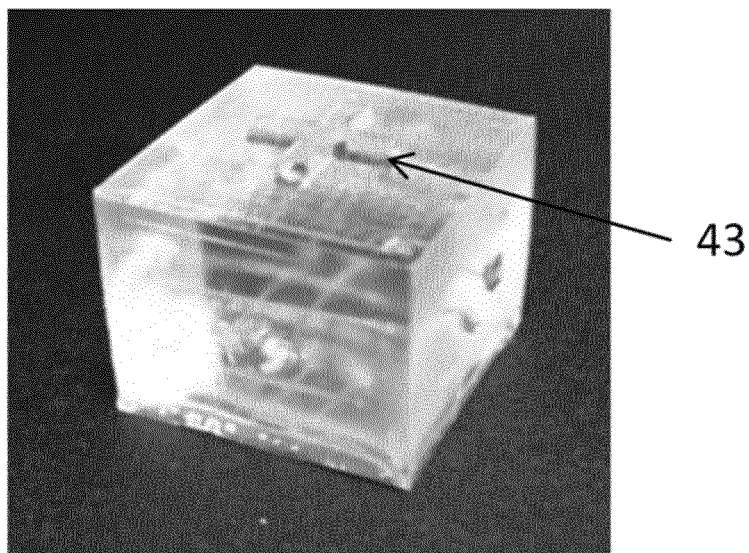
FIG. 4c displays an elastomer block comprising a protuberance forming a cross on a face of the elastomer block.

FIG. 4c displays an elastomer block comprising a protuberance 43 on a face of the elastomer block, the cross being visible to the naked eye and forming a cross. The protuberance may help defining if the ultrasound transducer is rightly calibrated, evaluating the three-dimensional shape and position of a real cavitation region with the naked eyes through this protuberance.

The protuberances of the elastomer block and the graduation elements, being wires or markers, may be used together so as to help testing the ultrasound transducer.

As illustrated on FIGS. 3, 4a, 4b and 4c, the elastomer block is homogeneous and does not comprise elements which would, during the use of an ultrasound transducer, change coloration or liquefy due to a change of temperature, light radiation or pH variation. Particularly, the elastomer block does not comprise leuco-dye or other encapsulated dye which by their effusion, when cavitation bubbles are generated, may not exactly reflect the shape of the cavitation cloud generated and therefore a real cavitation region.

Typically, the ultrasound transducer is configured to operate at a frequency ranging from 100 kHz to 10 MHz, and even more preferably from 500 kHz to 2.5 MHz, with high intensity pulsed ultrasound emissions of a duration ranging from 0.1 to 50 µs, and even more preferably from 1 to 20 µs, delivered at a pulse repetition frequency ranging from 1 Hz to 1000 Hz, and even more preferably from 50 to 500 Hz, during a total test time of 10 to 180 seconds.

In the system of the present invention, the ultrasound transducer is mounted on a support structure so as for the ultrasound transducer to be within the acoustic coupling medium or acoustically coupled with the volume of an ultrasound-transmitting medium. Typically, when the volume of an ultrasound-transmitting medium is liquid or semi-liquid, the support structure extends from the outside of the vessel to the inside of the vessel and in particular in the acoustic coupling medium so as to support at least the ultrasound transducer in the acoustic coupling medium. However, the support structure may have different shapes and may be comprised partially or entirely in the vessel and/or in the acoustic coupling medium. In other embodiments, the support structure is not comprised in the volume of an ultrasound-transmitting medium and supports the ultrasound transducer so as for the ultrasound transducer to be acoustically coupled with the volume of an ultrasound-transmitting medium. In another particular embodiment, the support structure is a robotic arm which allows placing the ultrasound transducer in the acoustic coupling medium or so as to be acoustically coupled with the volume of an ultrasound-transmitting medium.

The method of the invention comprises a step of placing an elastomer block at an expected cavitation region of the ultrasound transducer. The elastomer block is typically placed so as for the expected cavitation region to correspond to a central part in the bulk of the elastomer block however the elastomer block may be placed so as for the expected cavitation region to correspond to a peripheral part in the bulk of the elastomer block.

The method of the invention comprises a step of activating the ultrasound transducer so as to generate cavitation bubbles in the elastomer block. The activation of the ultrasound transducer typically corresponds to the emission of repeated pulses at a single frequency and during a specific time however the activation may also correspond to one or more sequences of emission of pulses at same or different frequencies, the sequences having the same or different durations.

The method of the invention comprises a step of detecting in the elastomer block marks corresponding to the generated cavitation bubbles. The detection typically corresponds to a step of seeing with the naked eye if marks are present in the elastomer block, which correspond to cavitation bubbles which have been generated in the elastomer block. In particular embodiments where the elastomer block may be removed from the volume of ultrasound-transmitting medium, for instance when the elastomer block is disposed in a solid block with an opening for replacing the elastomer block, the elastomer block is removed from the volume of ultrasound-transmitting medium after activating the ultrasound transducer and prior to detecting in the elastomer block marks.

Alternatively, the step of detecting corresponds to a step of seeing by means of medical imaging, e.g. ultrasound imaging, computed tomography or magnetic resonance imaging, if marks are present in the elastomer block, which correspond to cavitation bubbles which have been generated in the elastomer block.

The method of the invention comprises deducing from the marks in the elastomer block a real cavitation region position of the ultrasound transducer. The step of deducing from the marks a real cavitation region may comprise the use of graduation elements, for instance by determining the centroid of the marks formed by the cavitation bubbles generated.

The method may comprise further identifying a difference between the localizations of the expected cavitation region and a real cavitation region. If a difference between the localizations is identified, the method may comprise further modifying the configuration of the ultrasound transducer so as for the expected cavitation region and a real cavitation region to have the same localizations. Also, if a difference between the localizations is identified, the method may comprise further modifying the expected cavitation region so as to correspond with a real cavitation region.

The method of the invention allows testing an ultrasound transducer able to cause the generation of cavitation bubbles. Testing an ultrasound transducer ensures that the use of the ultrasound transducer will generate cavitation bubbles at the expected cavitation region, e.g. that the expected cavitation region corresponds to a real cavitation region of the ultrasound transducer.

PARTICULAR EXAMPLES

Example 1

The elastomer block corresponds to the mix of 4,4' Methylenedicylohexyl diisocyanate (A) with a modified aliphatic diisocyanate (B) at a ratio of 1:1 by volume with a cure time of 16 hours at 23° C. The resulting elastomer block has a Shore hardness A of 30, a tensile strength of 5 MPa and its color is transparent clear. Such elastomer block is placed within a solid block of urethane through an opening on a first face of the solid block and the solid block is coupled to a transducer via a second face of the solid block which is mechanically adapted to receive the transducer. Such second face has for instance a shape which is complementary to the transducer, e.g. a concave face if the transducer has a convex face. The second face comprises an access port which allows ultrasonic waves to pass. The elastomer block has a thickness of 2 cm.

The transducer is activated at a central frequency of 1 MHz, at a Pulse Repetition Frequency (PRF) of 100 Hz and with 10 oscillations during 120 seconds. After the activation of the transducer, the elastomer block is optionally removed and the marks are assessed. Permanent marks with a conic shape are visible and therefore the shape of the cavitation cloud may be assessed. From the cavitation marks, a real cavitation region of the transducer may be deduced and is compared with the expected cavitation region so as to determine if the transducer needs to be calibrated.

Example 2

The elastomer block corresponds to the mix of 4,4' Methylenedicylohexyl diisocyanate (A) with phenylmercury neodecanoate (B) at a ratio (A:B) of 1:1.5 by weight with a cure time of 16 hours at 23° C. The resulting elastomer block has a Shore hardness A of 95, a tensile strength of 17 MPa and its color is transparent clear. The elastomer block has a thickness of 1.9 cm. The transducer is activated at a central frequency of 1 MHz, at a PRF of 100 Hz and with 10 oscillations during 180 seconds. After the activation of the transducer, the elastomer block is optionally removed and the cavitation cloud is assessed. Permanent cavitation marks with a grain of rice shape are visible and therefore the shape of a real cavitation region may be assessed. From the cavitation marks, a real cavitation region of the transducer may be deduced and is compared with the expected cavitation region so as to determine if the transducer needs to be calibrated.

Example 3

The elastomer block corresponds to water clear silicone having a Shore hardness A of 33 and which color is transparent clear. The elastomer thickness is 1.8 cm. The transducer is activated at a central frequency of 700 kHz, at a PRF of 70 Hz and with 10 oscillations during 60 seconds. After the activation of the transducer, the elastomer block is optionally removed and a real cavitation region is assessed. Permanent marks with a grain of rice shape are visible and therefore the shape of the cavitation marks may be assessed. From the cavitation marks, a real cavitation region of the transducer may be deduced and is compared with the expected cavitation region so as to determine if the transducer needs to be calibrated.

Example 4

In another particular embodiment, the elastomer block corresponds to water clear silicone having a Shore hardness A of 30 and which color is clear amber. The elastomer block thickness is 1.5 cm. The transducer is activated at a central frequency of 700 kHz, at a PRF of 70 Hz and with 10 oscillations during 60 seconds. After the activation of the transducer, the elastomer block is optionally removed and the cavitation mark is assessed. Permanent marks with a grain of rice shape are visible and therefore the shape of the cavitation cloud may be assessed. From the cavitation mark, a real cavitation region of the transducer may be deduced and is compared with the expected cavitation region so as to determine if the transducer needs to be calibrated.

Example 5

In another particular embodiment, the elastomer block corresponds to polyurethane matrix having a Shore hardness D of 80 and which color is clear yellow. The elastomer block thickness is 2 cm. The transducer is activated at a central frequency of 700 kHz, at a PRF of 100 Hz and with 10 oscillations during 95 seconds. After the activation of the transducer, the elastomer block is optionally removed and the cavitation mark is assessed. Permanent marks with an oval shape are visible and therefore the shape of the cavitation cloud may be assessed. From the cavitation mark, a real cavitation region of the transducer may be deduced and is compared with the expected cavitation region so as to determine if the transducer needs to be calibrated.

The examples described above are given as illustrations of embodiments of the invention. They do not in any way limit the scope of the invention which is defined by the following claims.

The invention claimed is:

1. A method of testing the accuracy and the performance of an ultrasound transducer able to generate cavitation bubbles, comprising:
   placing in a volume of an ultrasound-transmitting medium an elastomer block at an expected cavitation region of the ultrasound transducer;
   activating the ultrasound transducer so as to generate cavitation bubbles in the elastomer block;
   detecting in the elastomer block marks corresponding to the generated cavitation bubbles; and
   deducing from the marks the three-dimensional characteristics of a real cavitation region of the ultrasound transducer.

2. The method of claim 1, the elastomer block having a total optical transmittance of at least 20%.

3. The method of claim 1, the method comprising a step of verifying the correct alignment of one or more imaging systems with the ultrasound transducer.

4. The method of claim 1, the elastomer block comprising a material chosen among a silicone, urethane, polyurethane or a combination thereof.

5. The method of claim 1, the elastomer block having a hardness comprised between Shore hardness 10A and Shore hardness 80D.

6. The method of claim 1, further comprising a plurality of graduation elements embedded in the elastomer block, said graduation elements being resistant to distortion or mechanical damage by the generated cavitation bubbles.

7. The method of claim 6, the graduation elements being wires or markers visible to the naked eye and/or visible with imaging modalities.

8. The method of claim 1, wherein the ultrasound-transmitting medium is liquid or semi-liquid and contained within a vessel.

9. The method of claim 1, the volume of ultrasound-transmitting medium forming a solid block comprising an access port, the access port being adapted for exposing a portion of a surface of the elastomer block to ultrasounds emitted by the ultrasound transducer.

10. The method of claim 9, the solid block further comprising at least one opening, the at least one opening being adapted for seeing and/or replacing the elastomer block.

11. A system comprising:
   a volume of an ultrasound-transmitting medium comprising an acoustic coupling medium,
   an elastomer block being disposed in the volume of an ultrasound-transmitting medium, and
   an ultrasound transducer, the ultrasound transducer being mounted on a support structure so as for the ultrasound transducer to be within the acoustic coupling medium or acoustically coupled with the volume of an ultrasound-transmitting medium.

12. The system of claim 11, further comprising one or more imaging systems.

13. The system of claim 11, the ultrasound-transmitting medium being liquid or semi-liquid and contained within a vessel.

14. The system of claim 11, the volume of ultrasound-transmitting medium forming a solid block comprising an access port, the access port being adapted for exposing a portion of a surface of the elastomer block to ultrasounds emitted by the ultrasound transducer.

15. The system of claim 14, the solid block further comprising at least one opening, the at least one opening being adapted for seeing and/or replacing the elastomer block.

16. The system of claim 14, wherein, at a temperature of 25° C. and a pressure of 1 atm, the speeds of sound in the volume of ultrasound-transmitting medium and in the elastomer block are comprised between 500 m·s$^{-1}$ and 2500 m·s$^{-1}$ and are no more than 10% different, and/or wherein the acoustic impedances of the material of the solid block and the elastomer block are comprised between 0.5 MRayl to 2.5 MRayl and are no more than 10% different.

17. The system of claim 11, further comprising a plurality of graduation elements embedded in the elastomer block, said graduation elements being resistant to distortion or mechanical damage by the generated cavitation bubbles.

\* \* \* \* \*